(12) United States Patent
Moffett et al.

(10) Patent No.: US 6,379,940 B2
(45) Date of Patent: Apr. 30, 2002

(54) STABLE COMPOSITION COMPRISING A NUCLEASE AND A PHOSPHATASE

(75) Inventors: Robert B. Moffett, Shaker Heights; Jeannine Muller-Greven, Mentor, both of OH (US)

(73) Assignee: USB Corporation, Cleveland, OH (US)

( * ) Notice: Subject to any disclaimer, the term of this patent is extended or adjusted under 35 U.S.C. 154(b) by 0 days.

(21) Appl. No.: 09/812,808

(22) Filed: Mar. 20, 2001

Related U.S. Application Data

(60) Provisional application No. 60/190,813, filed on Mar. 21, 2000.

(51) Int. Cl.$^7$ .............................. C12N 9/96; C12P 19/34
(52) U.S. Cl. ...................... 435/188; 435/91.2; 435/187; 435/199; 514/2
(58) Field of Search ........................... 435/6, 188, 194, 435/187; 514/2

(56) References Cited

U.S. PATENT DOCUMENTS

| | | |
|---|---|---|
| 4,720,458 A | 1/1988 | Sullivan et al. |
| 5,741,676 A | 4/1998 | Fuller |
| 5,756,285 A | 5/1998 | Fuller |
| 6,121,023 A | 9/2000 | Romano et al. ......... 435/91.21 |

OTHER PUBLICATIONS

Werle E. et al. Convenient single–step, one tube purification of PCR products for direct sequencing. Nucleic Acids Research, 22(20): 4354–4355, 1994.*
Ragnar L. Olsen et al., Alkaline Phosphatase From The Hepatopancreas Of Shrimp (*Pandalus Borealis*): A Dimeric Enzyme With Catalytically Active Subunits, Comp. Biochem. Physiol., vol. 99B, No. 4, pp. 755–761 (1991).
PCR Product Pre–Sequencing Kit, protocol booklet, USB Corporation 1999.
Biotec–Mackzymal AS, Shrimp Alkaline Phosphatase, dated prior to Mar. 20, 2001.
USB Corporation, Sequenase Version, 2.0 PCR Product Sequencing Kit, booklet, 1999.

* cited by examiner

Primary Examiner—Jeffrey Fredman
Assistant Examiner—Suryaprabha Chunduru
(74) Attorney, Agent, or Firm—Pearne & Gordon LLP

(57) ABSTRACT

A composition containing a nuclease, preferably Exonuclease I, and a phosphatase, preferably Shrimp Alkaline Phosphatase, wherein the enzymes are combined in a single composition yet each enzyme retains significant functional activity over time. Combining Exonuclease I and Shrimp Alkaline Phosphatase into one composition allows simplified processing of amplified DNA to degrade residual primers and nucleotide triphosphates thereby facilitating subsequent DNA analysis.

50 Claims, No Drawings

US 6,379,940 B2

STABLE COMPOSITION COMPRISING A NUCLEASE AND A PHOSPHATASE

This application claims the benefit of U.S. Provisional Patent Application Ser. No. 60/190,813, filed Mar. 21, 2000.

BACKGROUND OF THE INVENTION

The invention relates to the field of processing DNA, specifically including amplified DNA, to remove residual primers or other unwanted single-stranded DNA and nucleotide triphosphates prior to performing other operations, such as, but not limited to, DNA sequencing, SNP analysis, or gene expression analysis.

Exonuclease I (Exo I) digests single-stranded DNA in a 3'→5' direction producing 5' mononucleotides. This enzyme is particularly useful in preparing amplified DNA products, such as PCR products, for sequencing. It degrades residual primers from the amplification reaction that would otherwise be carried over into the sequencing reaction. U.S. Pat. Nos. 5,741,676 and 5,756,285 generally disclose methods for DNA sequencing via amplification, both of which are hereby incorporated herein by reference. (See also R. L. Olsen et al., Comp. Biochem. Physiol., vol. 99B, No. 4, pp. 755–761 (1991)).

Amplification primers carried over into a sequencing reaction could act as sequencing primers and generate sequencing reaction products, thereby creating a background of secondary sequences which would obscure or interfere with observing the desired sequence. Both the concentration and specific activity (purity) of commercially available Exonuclease I may vary over a wide range. Commonly the enzyme is manufactured to a specific activity between 50,000 and 150,000 units of enzyme per mg and supplied for the purpose of processing amplified DNA at a concentration around 10 units per microliter. Enzyme with either higher or lower specific activity and either more or less concentrated could be employed in the described applications by suitable alterations in the applied protocol, such as adding less or more volume (or amount) of enzyme, respectively.

The storage buffer of commercially available Exonuclease I is: 20 mM Tris-HCl, pH 7.5; 0.5 mM EDTA; 5 mM 2-mercaptoethanol; 50 vol. % glycerol, made up in water (major manufacturer and supplier, USB Corporation, Cleveland, Ohio, USA).

Alkaline Phosphatases, as exemplified by Shrimp Alkaline Phosphatase (SAP) and Calf Intestinal Alkaline Phosphatase (CIP), catalyze the hydrolysis of 5'-phosphate residues from DNA, RNA, and ribo- and deoxyribonucleoside triphosphates (dNTPs or nucleotide triphosphates). SAP is particularly useful in preparing amplified products, such as PCR products, for sequencing because it can readily be inactivated by heat prior to performing a sequencing reaction. SAP degrades residual dNTPs from the amplification reaction. If residual dNTPs are carried over from the amplification reaction to the sequencing reaction, they add to, and thereby alter, the concentration of dNTPs in the sequencing reaction in an indeterminant and non-reproducible fashion. Since, within narrow limits, high quality sequencing requires specific ratios between the sequencing reaction dNTPs and ddNTPs, an alteration in the concentration of dNTPs may result in faint sequencing reaction signals.

The sole manufacturer of SAP has produced enzyme with a wide range of specific activities and concentrations. Examples include batches of enzyme with concentrations ranging from 4.2 units/μl to 13.9 units/μl with specific activities not being reported. Enzyme with either higher or lower specific activity and either more or less concentrated could be employed in the described applications by suitable alterations in the applied protocol such as adding less or more volume (or amount) of enzyme, respectively. The storage buffer of commercially available Shrimp Alkaline Phosphatase, the preferred enzyme for the above described application, is: 25 mM Tris-HCl, pH 7.5; 1 mM $MgCl_2$; 0.1 mM $ZnCl_2$; 50 vol. % glycerol, made up in water (available from USB Corporation, Cleveland, Ohio, USA).

Prior to sequencing or other analyses, Exo I and SAP are frequently used to process PCR reaction products. Currently each enzyme is supplied in its own storage buffer as described above. In a recommended procedure (see "PCR Product Pre-Sequencing Kit" protocol booklet, USB Corporation) one microliter of each enzyme preparation is independently added (via pipetting) to 5 microliters of PCR reaction product. In this application multiple pipetting steps potentially can introduce significant experimental error, both determinant and indeterminant, into subsequent sequencing measurements. Furthermore, the ratio of Exo I to SAP can vary significantly among subsequent experiments due to delivery of imprecise relative volumes of each of the enzyme preparations to subsequent batches of amplified DNA.

Historically, a stable composition comprising both enzymes in fixed proportion has not been commercially produced. It may have been thought that the $MgCl_2$ and $ZnCl_2$, both present in the commercial SAP storage buffer, were incompatible with the EDTA present in the commercial Exo I storage buffer. EDTA is a chelating agent that reacts strongly with $Mg^{2+}$ and $Zn^{2+}$ ions. When mixed together such that the EDTA is in molar excess, the EDTA effectively sequesters $Mg^{2+}$ and $Zn^{2+}$ ions thereby preventing these ions from interacting with any protein(s) present in the solution. As a class, alkaline phosphatases are considered to be multimeric, metallo-enzymes that require a divalent ion, frequently $Zn^{2+}$, for structural stability and activity.

Consequently, there is a need in the art for a stable composition comprising both enzymes in a single delivery vehicle. Preferably, such a stable composition will enjoy a long shelf life, each enzyme retaining a significant proportion of its original functional activity over time.

SUMMARY OF THE INVENTION

A composition comprising a nuclease and a phosphatase is provided. The composition is substantially free from the presence of amplified deoxyribonucleic acid. The phosphatase in the composition retains at least 50% of its functional activity when the composition is stored at 4° C. for 24 hours. A method of degrading preselected nucleic acids present in a sample of material is also provided. The method comprises the step of contacting the sample with a composition comprising a nuclease and a phosphatase.

DETAILED DESCRIPTION OF THE PREFERRED EMBODIMENTS OF THE INVENTION

As used herein, when a range such as 5–25 or 5 to 25 or between 5 and 25 is given, this means preferably at least 5 and, separately and independently, preferably not more than 25.

As used herein, and in the appended claims, when the concentration of a component is provided as a volume/volume percent (% v/v), this means that that component is present by volume in a proportion relative to the total volume of the composition (including all of its constituent components) equal to the stated percent for the specific component. By way of example, a composition with 50% v/v of glycerol is composed of a volume of glycerol equal to one half (or 50%) of the total volume of the composition including all of its components (including glycerol and water if present). In such a composition, concentrations reported in molarity (M) are based upon the total volume of the composition including all of its components.

As used herein, one unit of nuclease (e.g. Exo I) enzyme is that amount of nuclease enzyme required to catalyze the release of 10 nmol of acid-soluble nucleotide from denatured DNA in 30 minutes at 37° C. under standard conditions.

As used herein, one unit of phosphatase (e.g. SAP) enzyme is that amount of phosphatase enzyme required to catalyze the hydrolysis of 1 $\mu$mol of p-nitrophenylphosphate per minute in glycine/NaOH buffer (pH 10.4) at 37° C.

As used herein, the term "functional activity" generally refers to the ability of an enzyme to perform its designated function as described below. As used herein, the functional activity of nuclease (e.g. Exo I) is qualitatively defined in terms of the ability of nuclease enzyme to degrade residual PCR primers from PCR amplified DNA to a level low enough so as not to materially interfere with subsequent sequencing reactions or other applications. The functional activity of nuclease is measured for Exo I using the following methodology. 1 $\mu$l of a solution containing Exo I is added to 5 $\mu$l of PCR amplified DNA and the mixture incubated at 37° C. for 15 minutes. The reaction is terminated by heating to 80° C. for 15 minutes. The treated DNA is then used as a template in a standard sequencing reaction, such as the USB T7-Sequenase V2.0 PCR Product Sequencing Kit, and the quality of the sequencing ladder examined to determine the effectiveness of degrading residual primers from the amplified DNA. Exo I, as commercially supplied by USB Corporation for this application, can be used between 0.5 and 20 units, preferably 1–15 units, more preferably at about 10 units per 5 $\mu$l reaction product in standard pre-sequencing processing of PCR amplification product. Quantitatively, the functional activity and half-life of Exo I and other nucleases of the invention are ascertained after a specified period of storage at a specified temperature as described in the following paragraph.

Original Exo I composition containing 10 units Exo I/$\mu$l is prepared at time zero, and a serial dilution performed, such that the concentration of enzyme in each successive dilution is one half that of the prior dilution, for a total of preferably 5 dilutions plus the original undiluted composition. This results in the following: original undiluted composition, one half dilution, one quarter dilution, one eighth dilution, one sixteenth dilution, and one thirty-second dilution. Presuming no change in activity, the enzyme equivalents per microliter of Exo I composition in each respective dilution (beginning with the undiluted composition) are: 10 units Exo I; 5 units Exo I; 2.5 units Exo I, 1.25 units Exo I, 0.625 units Exo I; and 0.3125 units Exo I; corresponding to the undiluted composition, as well as dilutions equal to one half, one fourth, one eighth, one sixteenth, and one thirty-second the concentration of the undiluted composition. At time zero, 1 $\mu$l of each of the above is separately delivered to a separate 5 $\mu$l sample of a control PCR reaction product (which has been pretreated or is being co-treated to materially degrade the dNTPs) containing residual DNA primers to be degraded prior to sequencing, and the enzyme is permitted to degrade the residual primers. The sequencing is then performed and the sequence ladders (six in this example) compared. In looking at the sequence ladders or lanes, the first dilution where the sequencing ladder exhibits material secondary and/or multiple lane signals compared to the primary sequencing signal indicates that the enzyme activity dropped off at that dilution. This is referred to as the "drop-off dilution". This is used as a measuring stick or baseline for determining, at a subsequent point in time, the half-life and functional activity of the enzyme. At each of several subsequent points in time after storage at a specified temperature, e.g. 24 hours, 2, 3, 5, 7, 14, 21, 30, 60, 90, etc., days, a similar serial dilution analysis is performed on a portion of the original stored composition, and the "drop-off dilution" is again ascertained. The first time that the "drop-off dilution" shifts from one dilution (for example, the one sixteenth dilution) to the prior dilution (for example, the one eighth dilution) indicates the point in time that the half-life of the nuclease enzyme has been reached. For example, assume a serial dilution analysis was conducted every day and it took 7 days for the drop-off dilution to shift from the one sixteenth dilution to the one eighth dilution. This indicates that at 7 days, the enzyme has lost one half of its functional activity, because now, for the first time, it takes twice as much enzyme activity (the one eighth dilution is twice as concentrated as the one sixteenth dilution) to achieve the same result, i.e. full or material degradation of residual primer. Since it takes twice as much enzyme activity, the enzyme has reached its half-life.

For example, an original Exo I composition containing 10 units Exo I per 4$\mu$l is prepared and subject to serial dilution analysis as described above. It is found that the drop-off dilution is the one thirty-second dilution. The composition is then stored at 4° C. for a period of time, say one week. The stored composition is again subjected to serial dilution analysis, and the drop-off dilution remains the one thirty-second dilution. Serial dilution analyses are subsequently performed at 2, 3, 4, 5, etc., weeks, and it is found at the $5^{th}$ week test that, for the first time, the drop-off dilution is the one sixteenth dilution. This indicates that the half-life point has been reached. In this example, it can be seen that the half-life point was reached between the fourth and fifth weeks. Thus in this example, the nuclease enzyme in the composition retained at least 50% of its functional activity when the composition was stored for four weeks at 4° C.

As used herein, the functional activity of phosphatase (e.g. SAP) is qualitatively defined in terms of the ability of phosphatase enzyme to degrade residual PCR nucleotide triphosphates from PCR amplified DNA to a level low enough so as not to materially interfere with subsequent sequencing reactions or other applications. The functional activity of phosphatase is measured for SAP using the following methodology. 1 $\mu$l of a solution containing SAP is added to 5 $\mu$l of PCR amplified DNA and the mixture incubated at 37° C. for 15 minutes. The reaction is terminated by heating to 80° C. for 15 minutes. The treated DNA is then used as template in a standard sequencing reaction, such as the USB T7-Sequenase V2.0 PCR Product Sequencing Kit, and the quality of the sequencing ladder examined to determine the effectiveness of degrading residual nucleotide triphosphates from the amplified DNA. If residual nucleotide triphosphates in PCR amplified DNA are not effectively degraded, the nucleotide triphosphates from the PCR reaction will alter the ratio of dNTPs/ddNTPs in the sequencing reaction causing faint signals. Independently formulated SAP, as commercially supplied by USB Corporation for this application, can be used to degrade residual nucleotide triphosphates in PCR amplified DNA between 0.1 and 5 units, preferably 1–3 units, more preferably at about 2 units per 5 $\mu$l reaction product in standard pre-sequencing processing of PCR amplification product. Quantitatively, the functional activity and half-life of SAP and other phosphatases of the invention are ascertained via periodic serial dilution analyses similarly as explained above with respect to Exo I. An original SAP composition containing 2 units SAP per μl is prepared, and 1 μl of the original undiluted SAP composition and 5 serial dilutions thereof are delivered separately to separate 5 μl samples of a control PCR reaction product (preferably having been pretreated or being co-treated to degrade residual primers) having residual nucleotide triphosphates to be cleaned up, and the enzyme is permitted to degrade the nucleotide triphosphates. The sequencing is then performed and the sequence ladders compared as before. In looking at the sequence ladders or lanes, the first dilution where the first 50 bases of a DNA sequencing ladder having more than 200 discernable bases are materially fainter than in the prior dilution indicates that the enzyme activity dropped off at that dilution. This is referred to as the "drop-off dilution", and is used as a measuring stick or baseline for determining, at subsequent points in time, the half-life and functional activity of the enzyme. At each of several subsequent points in time after storage at a specified temperature, e.g. 24 hours, 2, 3, 5, 6, 14, 21, 30, 60, 90, etc., days, a similar serial dilution analysis is performed on a portion of the original stored composition, and the "drop-off dilution" is again ascertained. Half-life for SAP is then determined similarly as explained above with respect to Exo I.

For example, an original SAP composition containing 2 units SAP per μl is prepared and subject to a serial dilution analysis as described above. It is found that the drop-off dilution at time zero is the one thirty-second dilution. The composition is then stored at 4° C. for a period of time, say one week. The stored composition is then subjected to another serial dilution analysis, and the drop-off dilution remains the one thirty-second dilution. Serial dilution analyses are subsequently performed at 2, 3, 4, 5, etc., weeks, and it is found at the 5$^{th}$ week test that, for the first time, the drop-off dilution is the one sixteenth dilution. In this example, it can be seen that the half-life point was reached between the fourth and fifth weeks. Thus in this example the phosphatase enzyme in the composition retained at least 50% of its functional activity when the composition was stored for four weeks at 4° C.

Characteristics of the Preferred Compositions

The present invention relates to a single composition comprising both a nuclease and a phosphatase, wherein less than 50%, preferably less than 40%, preferably less than 30%, preferably less than 20%, preferably less than 10%, of the functional activity of each and/or either enzyme is lost per 24 hours, more preferably per week, even more preferably per month, and most preferably per 4 months, when held or stored under a specified condition such as −20° C., 0° C., +4° C., or room temperature (e.g. +20° C.).

The phosphatase in the composition preferably retains at least 50% of its functional activity when said composition is stored at 4° C. for 24, more preferably 36, more preferably 48, more preferably 60, more preferably 72, more preferably 96, hours. The nuclease in the composition preferably retains at least 50% of its functional activity when said composition is stored at 4° C. for 2, more preferably 3, more preferably 5, more preferably 7, more preferably 9, more preferably 12, more preferably 14, days. The invented composition is preferably substantially free from the presence of deoxyribonucleic acid, nucleic acid, amplified DNA, nucleotide triphosphates, oligonucleotides, and primers, each of which could interfere with the composition's performance.

Preferably, the nuclease is heat-labile, preferably single-stranded exonuclease, preferably Exonuclease 7 or RecJ, most preferably Exo I, and the phosphatase is preferably heat-labile, preferably eukaryotic phosphatase, preferably bacterial or animal phosphatase, preferably mammal phosphatase, most preferably SAP. The invented composition preferably is formulated in such a manner that when an aliquot of 2 μl of the composition is contacted with 5 μl of PCR reaction product (DNA that was amplified by standard PCR techniques), the residual primers and nucleotide triphosphates are effectively inactivated or degraded by being decreased to a level that allows effective sequencing of the amplified product. The amounts and concentrations of the Exo I, SAP and other materials may vary depending upon the specific nature and amount of the amplified DNA product, the nature and amount of residual primers and nucleotide triphosphates, the time and temperature of the processing reaction, and the sequencing method used. Embodiments of the invention also allow for adding different volumes or proportions of the combined composition as needed to achieve the desired result. Further embodiments allow the composition containing nuclease, such as Exo I, and phosphatase, such as SAP, to be dehydrated or dried (or optionally lyophilized), thus comprising at most 10 wt. % water, and these concentrated or dried forms to be contacted with the amplified DNA.

The invention provides a nuclease and a phosphatase in a single composition. The composition can be used for degrading residual materials present in the product of a nucleic acid synthesis reaction, examples of which are referenced or described in this paragraph. The method involves contacting (for example, mixing) the reaction product with the composition. The composition can be used for cleaning up or degrading residual primers and residual nucleotide triphosphates, preferably after a DNA or RNA amplification reaction, preferably a PCR or RT-PCR amplification reaction, alternatively an isothermal amplification reaction. The composition can also be used for cleaning up a nucleic acid (preferably DNA) replication reaction, such as primer-initiated RNA or DNA synthesis. After such degrading of the residual materials in the reaction product, the cleaned-up reaction product can be used in subsequent analyses, such as DNA sequencing, less preferably SNP (Single Nucleotide Polymorphism) analysis (which is a way of determining single nucleotide differences), other genetic analyses (including gene expression) or other analyses of nucleic acids where cleanup of residual primers, residual oligonucleotides and/or residual nucleotide triphosphates is useful, such as analysis of multiple base additions, deletions or differences.

The invented composition can also be used, with or without additional nucleases and/or phosphatases, to act as a selective and/or all-purpose clean-up composition to clean up samples other than amplification reaction products, such as a biological sample such as biopsy materials, blood samples, bodily fluids, or intermediates used in the production of biological materials. In such a case the composition containing a nuclease and a phosphatase would degrade preselected nucleic acids present in the sample of material. The sample could be material, such as biopsy material, isolated from biological material, such as a human body.

With respect to the disclosure of this invention the referenced stability generally relates to compositions held in either liquid or dried states. However, it is recognized that combinations of Exo I and SAP can be stored frozen. In this case if frozen quickly enough and held at a low enough temperature compositions of Exo I and SAP could be held with potentially little reduction in functional activity or performance for extended periods of time such as at least 6, 12, 24, 36, 60 or 100 months. Preferably the invented composition retains at least 10, 20, 30, 40, 50, 60, 70, 80 and/or 90% of its functional activity for each enzyme following storage of the composition for 24 hours, or 2, 3, 4, 5, 8, 10, 15, 20, 30, 40, 60, 80, 100, 120, 150, 180, 210, 240, 300, 360, 500, 1000, 1500, 2000 and/or 3000 days at 25° C., 20° C., 18° C., 10° C., 4° C., 0° C., −10° C., −20° C., −30° C., −40° C., −60° C., −80° C., −100° C., −150° C. or −190° C. The invented compositions are packaged, stored, shipped and used as known in the art.

Preferred Compositions

The only necessary components of the invented composition are the enzymes, that is, the nuclease and the phosphatase. The other components described herein are preferred but are optional. The nuclease is preferably Exonuclease I (Exo I) and the phosphatase is preferably alkaline phosphatase, preferably Shrimp Alkaline Phosphatase (SAP) as indicated above. The combination of enzymes can be supplied in dried form or, more preferably, in a liquid, preferably in an aqueous solution. Preferred aqueous solutions are described herein. Less preferably, the enzymes can be supplied in more concentrated solutions, such as solutions (with or without the optional components) which are at least 2, 3, 4, 5, 6, 8, 10, 15, 20, 30, 50, 80, 100, 150, 200, 300, 500, 800, 1,000, 2,000, 5,000, 8,000, or 10,000 times more concentrated than the solutions described herein, or concentrated all the way to dryness. Diluted solutions can also be provided. In the invented composition, any preferred or less preferred concentration or range of any component can be combined with any preferred or less preferred concentration or range of any of the other component or components; it is not required or necessary that all or any of the components or concentrations or ranges be that which is most preferred.

Preferably, the composition is a liquid, preferably aqueous, combination of a nuclease and a phosphatase (preferably an alkaline phosphatase), preferably Exo I and SAP, where the Exo I to SAP unit ratio is between 1:5000 and 5000:1, more preferably between 1:500 and 500:1, even more preferably between 1:50 and 50:1 and most preferably between 1:10 and 10:1 with a total protein concentration ranging from 1 µg/ml to 200 mg/ml, more preferably 10 µg/ml to 100 mg/ml, even more preferably 100 µg/ml to 50 mg/ml and most preferably between 1.0 mg/ml and 10 mg/ml. With such a combination of Exo I and SAP the units of Exo I contacted with 5 µl PCR amplified DNA could range from 0.01 to 100 units of Exo I, more preferably 0.1 to 30 units of Exo I, even more preferably 1 to 15 units of Exo I and most preferably 10±4 units of Exo I, the 5 µl PCR amplification reaction product is also preferably contacted with 0.01 to 100 units of SAP, more preferably 0.1 to 10 units of SAP, even more preferably 0.5 to 5 units of SAP and most preferably 2±1 units of SAP. Optionally, other alkaline phosphatates, such as calf intestinal alkaline phosphatase, may be used in place of the SAP. The concentration of nuclease in the invented composition is preferably at least 0.01, 0.1, 1, 2, or 5 units of nuclease enzyme per microliter. The concentration of phosphatase in the invented composition is preferably at least 0.01, 0.1, 1, 2, or 5 units of phosphatase enzyme per microliter.

In the invented composition preferably the pH is between 4.0 and 12.0, more preferably between pH 6.0 and 10.0, more preferably between 7.0 and 9.0, more preferably less than 8, more preferably between 7 and 8, and most preferably pH 7.5±0.2 or pH 7.5±0.3, preferably controlled by a buffer. The invented composition may optionally and preferably contain a buffer at a concentration of zero to 250 mM, more preferably between 5 mM to 100 mM, even more preferably between 15 mM to 50 mM and most preferably 25±5 mM, preferably of Tris-HCl, preferably at pH 7.5 to pH 8.5 or the pH ranges mentioned above. Other buffers may be used such as, but not limited to: organic buffers such as MOPS, HEPES, TRICINE, etc., or inorganic buffers such as Phosphate or Acetate. Buffers or other agents may be added to control the pH of the solution thereby increasing the stability of the enzymes.

The invented composition may optionally and preferably contain a reducing agent such as but not limited to: dithiotreitol (DTT) or 2-mercaptoethanol; preferably zero to 100 mM, more preferably 0.1 mM to 50 mM, even more preferably 0.5 to 10 mM and most preferably 1.0±0.2 mM. Reducing agents may be added to limit enzyme oxidation that might adversely affect stability of the enzymes.

The invented composition may optionally and preferably contain monovalent ions such as, but not limited to: $Na^+$, $K^+$, $Li^+$, $Cl^-$, $Br^-$ or acetate ($HCO_2^-$) at a concentration of zero to 500 mM, more preferably 0.5 mM to 100 mM, even more preferably 1 mM to 50 mM and most preferably 1 to 10 mM. The presence of monovalent ions can help prevent protein precipitation which might lead to inactivation; addition of other compounds such as chelating agents frequently lead to the addition of trace amounts of monovalent ions.

The invented composition may optionally and preferably contain a complexing or chelating agent such as, but not limited to, $Na_2$-EDTA or $Na_2$-EGTA at a concentration of zero to 100 mM, more preferably 0.05 to 10 mM, even more preferably 0.1 to 2 mM, and most preferably 0.5±0.1 mM. Chelating agents are frequently added to protein solutions to sequester metal ions which if present can catalyze changes in amino acid side chain chemistry and under certain conditions cause breaks in the amino acid backbone of enzymes, thereby decreasing activity.

The invented composition may optionally contain an amino acid based carrier or stabilizer such as, but not limited to, bovine serum albumin and Poly L-lysine, preferably at a concentration between zero and 100 mg/ml, more preferably between 0.01 and 10 mg/ml and most preferably between 0.1 and 1.0 mg/ml.

The invented composition may optionally contain divalent ions such as but not limited to: $Zn^{2+}$, $Mg^{2+}$, $Co^{2+}$, $Mn^{2+}$ and/or $Ca^{2+}$, preferably at a concentration between zero and 200 mM, more preferably between zero and 20 mM, more preferably between 0.0001 mM and 5 mM and most preferably 0.002 to 1.0 mM. Divalent ions are preferred or required for effective enzyme activity of some proteins, such as phosphatases. Trace amounts of divalent ions may be present as a result of the addition of other substances to the composition; the normal composition of SAP contains both $Zn^{2+}$ and $Mg^{2+}$ which may accompany the enzyme into the composition.

The invented composition may optionally contain detergents (singly or in combination) such as, but not limited to, non-ionic, ionic or zwitterionic detergents added to stabilize the enzymes or enhance performance. For example Nonidet P40, Triton X100 or Tween 20 between zero and 20% v/v, more preferably between 0.01% and 5% v/v, and most preferably between 0.1% and 1.0% v/v. Similarly SDS, singly or in combination with other detergents, may be added between zero and 5% v/v, more preferably between 0.0001% and 1% v/v, and most preferably between 0.005% and 0.1% v/v.

The invented composition may optionally contain other chemicals added that enhance performance such as, but not limited to, DMSO between zero and 50% v/v, more preferably between 0.001% and 10% v/v, most preferably between 0.01% and 1% v/v.

The invented composition may optionally contain a dextran such as Dextran T-10 or Dextran T500 or other polysaccharide between zero and 50% v/v, more preferably between 0.1% and 10% v/v and most preferably between 1% and 5% v/v.

The invented composition may optionally and preferably contain an enzyme stabilizer or a material that inhibits ice formation such as, but not limited to, glycerol, ethylene glycol or glycine, preferably glycerol, preferably at a concentration of zero to 99% v/v, more preferably 1% to 75% v/v, more preferably 5% to 65% v/v, more preferably 20% to 60% v/v, more preferably 35% to 58% v/v, and most preferably 50±5% v/v.

The invented composition may optionally contain mono- or disaccharide such as glucose or maltose that may stabilize the enzymes or facilitate the composition of a dry embodiment. The mass of the mono- or disaccharide is preferably at least zero, 0.1, 1, 10, 100, 1000 or 10,000, or not more than 10 or 100 or 1000 or 10,000, times the mass of the protein in the composition.

The most preferred compositions according to the invention are described below as Compositions D and E. Composition D is preferred for manual pipetting operations, and composition E is preferred for automated pipetting operations. Where composition D is used, preferably 2 µl of composition D are combined with 5 µl of PCR reaction product to effectively degrade residual primers and nucleotide triphosphates prior to sequencing. Where composition E is used, preferably 5 µl of composition E are combined with 5–25 µl, preferably 5 µl, of PCR reaction product to effectively degrade residual primers and nucleotide triphosphates prior to sequencing or other analyses. Whether using composition D or E, it is preferred that 10 units of Exo I and 2 units of SAP are delivered to 5 µl of product containing residual primers and/or nucleotide triphosphates to be degraded.

Further aspects of the present invention will now be demonstrated, and the invention will be better understood in conjunction with the following examples, which describe preferred embodiments of the invention. The following examples are provided by way of illustration and not limitation, and it should be understood that other nuclease- and phosphatase-containing compositions comprising other combinations and concentrations of optional components are possible and intended.

EXAMPLES

In conjunction with the following experiments, 5 separate nuclease/phosphatase compositions were prepared, and are generally referred to herein as Compositions A through E. The compositions and component concentrations of each composition are provided below.

Composition A was prepared as an aqueous composition with the following components: 10 units/µl of Exonuclease I; 2 units/µl of Shrimp Alkaline Phosphatase; 25 mM Tris-HCl, pH 7.5; 0.5 mM $Na_2$-EDTA; 1 mM DTT; 50% v/v glycerol, made up in water. Concentrated stocks of Exo I and SAP were dialyzed against 25 mM Tris-HCl, pH 7.5; 0.5 mM $Na_2$-EDTA; 1 mM DTT; 50% v/v glycerol. Following dialysis the enzymes were combined in Composition A so that each microliter of Composition A contained 10 units of Exo I and 2 units of SAP. Enzyme activity assays as well as enzyme functional activity were measured, as indicated in table 1, after the composition was stored at −20° C., 4° C. and +25° C. for various lengths of time.

Composition B was prepared as an aqueous composition with the following components: 10 units/µl of Exonuclease I; 2 units/µl of Shrimp Alkaline Phosphatase; 25 mM Tris-HCl, pH 7.5; 100 µg/ml bovine serum albumin; 1 mM DTT; 1 mM $MgCl_2$; 0.1 mM $ZnCl_2$; 50% v/v glycerol, made up in water. Concentrated stocks of Exo I and SAP were dialyzed against 25 mM Tris-HCl, pH 7.5; 100 µg/ml bovine serum albumin; 1 mM DTT; 1 mM $MgCl_2$; 0.1 mM $ZnCl_2$; 50% v/v glycerol. Following dialysis the enzymes were combined in Composition B so that each microliter of Composition B contained 10 units of Exo I and 2 units of SAP. Enzyme functional activity was measured, as indicated in table 1, after the composition was stored at −20° C., 4° C. and +25° C. for various lengths of time.

Composition C was prepared as an aqueous composition with the following components: 10 units/µl of Exonuclease I; 2 units/µl of Shrimp Alkaline Phosphatase; formulated into 50 mM Tris-HCl, pH 8.3; 0.5 mM $Na_2$-EDTA; 1 mM DTT; 0.5% v/v Tween 20; 0.5% v/v Nonidet P-40, 50% v/v glycerol, made up in water. The composition was made by mixing the appropriate amount of Exo I and SAP, in their commercially available storage buffers, into Composition C. This composition thus contained small amounts of $MgCl_2$ and $ZnCl_2$ derived from the commercial SAP composition. Functional activity was measured, as indicated in table 1, after the composition was stored at −20° C., 4° C. or 25° C. for various lengths of time.

Composition D was prepared as an aqueous composition with the following components: 5 units/µl of Exonuclease I; 1 unit/µl of Shrimp Alkaline Phosphatase; formulated into 25 mM Tris-HCl, pH 7.5; 0.5 mM $Na_2$-EDTA; 1mM DTT; 50% v/v glycerol. This composition was made by mixing the appropriate amount of Exo I and SAP, in their commercially available storage buffers, into Composition D. Composition D thus contains traces of $MgCl_2$ and $ZnCl_2$ derived from the commercial SAP composition, and 2-mercaptoethanol derived from the Exo I composition. In order to deliver 10 units of Exo I and 2 units of SAP, a working volume of 2 µl of this enzyme mixture was used. Enzyme functional activity was measured, as indicated in table 1, after the composition was stored at −80° C., −20° C., 4° C., and 25° C. for various lengths of time. A freeze and thaw experiment was also performed.

Composition E was prepared as an aqueous composition with the following components: 2 units/µl of Exonuclease I; 0.4 units/µl of Shrimp Alkaline Phosphatase; formulated into 25 mM Tris-HCl, pH 7.5; 0.5 mM $Na_2$-EDTA; 1 mM DTT; 50% v/v glycerol. This composition was made by mixing the appropriate amount of Exo I and SAP, in their commercially available storage buffers, into Composition E. Composition E thus contains traces of $MgCl_2$ and $ZnCl_2$ derived from the commercial SAP composition, and 2-mercaptoethanol derived from the Exo I composition. In order to deliver 10 units of Exo I and 2 units of SAP, a working volume of 5 µl for this enzyme mixture is a convenient volume for addition to PCR reaction mixtures by robotic pipetters. Enzyme functional activity was measured, as indicated in table 1, after the composition was stored at −20° C. for various lengths of time.

The functional activity of each of the above nuclease/phosphatase compositions was determined at the various stated temperatures and after the stated elapsed times as described above and further as described below. A sample of each composition was removed as appropriate and a serial 1:1 dilution made into the respective composition, such that the concentration of enzyme in each successive dilution was one half that of the prior dilution. For Compositions A–C, presuming no change in activity, these enzyme equivalents per volume addition to the PCR reaction product (per μl of the enzyme composition) were: 10 units Exo I with 2 units SAP; 5 units Exo I with 1 unit SAP; 2.5 units Exo I with 0.5 units SAP; 1.25 units Exo I with 0.25 units SAP; 0.625 units Exo I with 0.125 units SAP; and 0.3125 units Exo I with 0.0625 units SAP. These amounts thus represented the respective undiluted compositions, as well as dilute compositions diluted to one half, one fourth, one eighth, one sixteenth, and one thirty-second the concentration of the respective undiluted compositions.

These serial dilutions resulted in concentration of enzyme that paralleled those made with untreated Exo I and SAP stock enzyme. Performance of the enzyme dilutions was then examined by the standard performance assay employing the USB T7-Sequenase V 2.0 PCR Product Sequencing Kit and using 1 μl of diluted composition per assay for Compositions A, B and C; 2 μl of diluted composition per assay for Composition D; and 5 μl of diluted composition for Composition E.

The functional activity of nuclease and phosphatase enzymes was determined as described above. The half-life of each composition was that point in time when either the nuclease (Exo I) or the phosphatase (SAP) in the composition reached its half-life, ie., had lost at least 50% of its functional activity. Tabular results are presented in table 1 of Example 1 below, with additional results and detailed explanation following in Examples 2–5.

Example 1

SUMMARY OF STABILITY DATA FOR COMBINED COMPOSITIONS A–E AT TEMPERATURES RANGING FROM −80° C. TO +25° C.

TABLE 1

Stability of Exo I and SAP in Compositions A–E

| | | Activity Half-Life | | | |
|---|---|---|---|---|---|
| Temp. (° C.) | Composition A | Composition B | Composition C | Composition D | Composition E |
| 25 | >12 hours | — | <<1 hour | >12 hours | — |
| 4 | >3 days | — | — | >3 days | — |
| −20 | >4 months | >5 weeks | <2 days | >4 months | >5 weeks |
| −80 | — | — | — | No detectible loss after 8 weeks | — |

The activity half-life as expressed in table 1 is that duration of storage required to observe a 50% reduction in functional activity of either the Exo I or the SAP in the composition.

Example 2

STABILITY AT −20° C. OF EXONUCLEASE I AND SHRIMP ALKALINE PHOSPHATASE ENZYMES IN A COMBINED COMPOSITION

Unexpectedly after 8 weeks of storage at −20° C., Compositions A, B and D showed significant retention in functional activity of either the Exonuclease I or shrimp alkaline phosphatase as compared to their respective control enzymes. Even more unexpectedly, upon formulation over a 100% gain in SAP functional activity was observed in the test of Compositions A and D, the compositions containing an excess of EDTA. In this test when only 0.25 units of commercially formulated SAP (a 1/8 dilution) were used to react amplified PCR DNA, the bottom of the DNA sequence ladder was faint. This indicates that when this amount of SAP was used not all the residual dNTPs from the amplification reaction were degraded. When SAP was combined with Exo I in either Composition A or D, a strong sequencing reaction was still obtained when only 0.125 units of SAP (a 1/16 dilution) were used to react with the amplified PCR DNA product. This result was particularly surprising because published characterizations of SAP (Oksen, et.al., 1991) would lead one to expect the enzyme to lose nearly all its activity. Composition B exhibits an unexpected retention in functional activity (see table 1), but did not exhibit the unexpected increase in activity exhibited by Compositions A and D. Composition E also unexpectedly exhibited significant retention in activity (see table 1).

Example 3

STABILITY AT +4° C. OF EXONUCLEASE I AND SHRIMP ALKALINE PHOSPHATASE ENZYMES IN A COMBINED COMPOSITION

Unexpectedly, considerable functional activity of SAP in Composition A and Composition D was retained following storage at +4° C. with less than 50% of its functional activity being lost in three days. (See table 1).

Example 4

STABILITY AT +25° C. OF EXONUCLEASE I AND SHRIMP ALKALINE PHOSPHATASE ENZYMES IN A COMBINED COMPOSITION

Unexpectedly, considerable functional activity of SAP in Composition A as well as Composition D was retained following storage at +25° C. with as much as 25% of the original functional activity being retained after one day of storage at +25° C. This retention of activity appears to be even greater than that reported for SAP when stored in its normal, commercially available composition ("Shrimp Alkaline Phosphatase", Monograph, Biotec-Mackzymal AS, Tromso, Norway).

Example 5

STABILITY AT −80° C. OF EXONUCLEASE I AND SHRIMP ALKALINE PHOSPHATASE ENZYMES IN COMBINED COMPOSITION D

Upon thawing after 8 weeks of storage at −80° C., Composition D exhibited no detectable loss of functional activity of either Exonuclease I or Shrimp Alkaline Phosphatase.

In addition to the most preferred components and component concentrations described above, combined nuclease/phosphatase compositions according to the invention can be prepared using other, less preferred components and component concentrations. Table 2 summarizes various components and component concentrations that can be used in the invented composition. In table 2, any preferred or less preferred or more preferred concentration or range of any component can be combined with any preferred or less preferred or more preferred concentration or range of any of the other components; it is not required or necessary that all or any of the concentrations or ranges come from the same column.

TABLE 2

Further Preferred Components for the Invented Composition

| Component/Property | Most Preferred | Less Preferred | Less Preferred | Least Preferred |
|---|---|---|---|---|
| Exo I (units to be added to 5 μl PCR reaction product) | 10 ± 4 units | 1–15 units | 0.1–30 units | 0.01–100 units |
| SAP (units to be added to 5 μl PCR reaction product) | 2 ± 1 units | 0.5–5 units | 0.1–10 units | 0.01–100 units |
| Composition pH | 7.5 ± 0.2 | 7.0–9.0 | 6.0–10.0 | 4.0–12.0 |
| Buffer (Tris-HCl, MOPS, HEPES, TRICINE, etc.) | 25 ± 15 mM Tris-HCl | 15–50 mM | 5–100 mM | 0–250 mM |
| Reducing Agents (DTT, B-ME) | 1.0 ± 0.2 mM DTT | 0.5–10 mM | 0.1–50 mM | 0–100 mM |
| Monovalent Ions ($Na^+$, $K^+$, $Li^+$, $Cl^-$, etc.) | Trace | 1–50 mM | 0.5–100 mM | 0–500 mM |
| Complexing/Chelating Agents ($Na_2$-EDTA, $Na_2$-EGTA, etc.) | 0.5 ± 0.1 mM $Na_2$-EDTA | 0.1–2.0 mM | 0.05–10 mM | 0–100 mM |
| Amino Acid Based Carrier (Bovine Serum Albumin, Poly 1-lysine, etc.) | 0 | 0–1.0 mg/ml | 0–10 mg/ml | 0–100 mg/ml |
| Divalent Ions ($Zn^{2+}$, $Mg^{2+}$, $Co^{2+}$, etc.) | 0.002–1.0 mM | 0.0001–5 mM | 0–20 mM | 0–200 mM |
| Nonionic Detergents (Nonidet P40, Triton X100, Tween 20, etc.) | 0 | 0.1%–1% v/v | 0.01%–5% v/v | 0–20% v/v |
| Zwitterionic Detergents (CHAPS, CHAPSO, etc.) | 0 | 0.01%–1% v/v | 0.005%–5% v/v | 0–20% v/v |
| Ionic Detergents (SDS, etc) | 0 | 0.005%–0.1% v/v | 0.00001%–1% v/v | 0–5% v/v |
| Other chemicals such as DMSO | 0 | 0.01%–1% v/v | 0.001%–10% v/v | 0–50% v/v |
| Polysaccharide/Dextran | 0 | 1%–5% v/v | 0.1%–10% v/v | 0–50% v/v |
| Stabilizer (glycerol, ethylene glycol, etc) | 50% ± 5% v/v | 5%–65% v/v 30%–70% v/v 40%–60% v/v | 1%–75% v/v 25%–75% v/v | 0–99% v/v 10%–90% v/v 20%–80% v/v |
| Mono- or disaccharide (glucose, maltose, etc.) | 0 | 10–10,000 X protein mass | 1–100 X protein mass | 0.1–10 X protein mass |
| Water | Balance water or 50% ± 5% v/v | 30%–70% v/v 40%–60% v/v | 25%–75% v/v 20%–80% v/v 10%–90% v/v | 3%–99% v/v 1%–99.5% v/v |

Although the hereinabove described embodiments of the invention constitute the preferred embodiments, it should be understood that modifications can be made thereto without departing from the scope of the invention as set forth in the appended claims.

What is claimed is:

1. A composition comprising a nuclease and a phosphatase, said composition being substantially free from the presence of amplified deoxyribonucleic acid, said nuclease being present in said composition in a concentration of at least 0.01 units of nuclease per microliter of composition, wherein said phosphatase retains at least 50% of its functional activity when said composition is stored at −20° C. for 24 hours.

2. A composition according to claim 1, said composition being substantially free from the presence of nucleic acid.

3. A composition according to claim 1, said composition being substantially free from the presence of nucleotide triphosphates and primers.

4. A composition according to claim 1, said composition comprising an effective amount of shrimp alkaline phosphatase.

5. A composition according to claim 1, said composition comprising an effective amount of Exonuclease I.

6. A composition according to claim 1, wherein said phosphatase is alkaline phosphatase.

7. A composition according to claim 1, wherein said nuclease is a single-stranded exonuclease.

8. A composition according to claim 1, said composition further comprising an effective amount of a buffering agent.

9. A composition according to claim 8, wherein said buffering agent is Tris-HCl.

10. A composition according to claim 1, said composition having a pH of 7 to 8.

11. A composition according to claim 1, said composition further comprising an effective amount of a reducing agent.

12. A composition according to claim 1, said composition further comprising an effective amount of a chelating agent.

13. A composition according to claim 1, said composition further comprising at least 20 volume percent of a stabilizer selected from the group consisting of glycerol, ethylene glycol and glycine.

14. A composition according to claim 1, wherein said nuclease is present in said composition in a concentration of at least 0.1 units of enzyme per microliter.

15. A composition according to claim 1, wherein said phosphatase is present in said composition in a concentration of at least 0.1 units of enzyme per microliter.

16. A composition according to claim 1, said composition, upon being added to a product of a PCR amplification reaction, effectively degrading residual primers and permitting effective DNA sequencing.

17. A composition according to claim 1, said composition, upon being added to a product of a PCR amplification reaction, effectively degrading residual nucleotide triphosphates and permitting effective DNA sequencing.

18. A composition according to claim 1, wherein said composition consists essentially of said nuclease and said phosphatase.

19. A composition comprising a nuclease and a phosphatase, said nuclease being present in said composition in a concentration of at least 0.01 units of nuclease per microliter of composition, wherein said phosphatase in said composition retains at least 50% of its functional activity when said composition is stored at 4° C. for 24 hours.

20. A composition according to claim 19, said nuclease in said composition retaining at least 50% of its functional activity when said composition is stored at 4° C. for 3 days.

21. A composition according to claim 4, wherein said shrimp alkaline phosphatase is effective to degrade residual nucleotide triphosphates in a PCR reaction product.

22. A composition according to claim 5, wherein said Exonuclease I is effective to degrade residual primers in a PCR reaction product.

23. A composition according to claim 1, wherein said phosphatase is shrimp alkaline phosphatase and is present in said composition in a concentration of 0.2 units shrimp alkaline phosphatase per microliter of said composition, and said nuclease is Exonuclease I and is present in said composition in a concentration of 1 unit Exonuclease I per microliter of said composition.

24. A composition according to claim 23, wherein said composition has a pH of about 7.5.

25. A composition according to claim 23, further comprising at least one component selected from the group consisting of Tris-HCl, EDTA and DTT.

26. A composition according to claim 25, comprising 25 mM Tris-HCl, 0.5 mM EDTA and 1 mM DTT.

27. A composition according to claims 23, further comprising at least 20 volume percent of a stabilizer selected from the group consisting of glycerol, ethylene, glycol, and glycine.

28. A composition according to claim 27, comprising at least 20 volume percent glycerol.

29. A composition according to claim 21, said composition having a pH of 7 to 9.

30. A composition according to claim 21, said composition having a pH of about 7.5.

31. A composition according to claim 21, further comprising Tris-HCl.

32. A composition according to claim 31, comprising 5–100 mM Tris-HCl.

33. A composition according to claim 21, further comprising EDTA in a concentration of less than 100 mM.

34. A composition according to claim 21, further comprising DTT in a concentration of less than 250 mM.

35. A composition according to claim 21, said composition further comprising at least 20 volume percent of a stabilizer selected from the group consisting of glycerol, ethylene glycol and glycine.

36. A composition according to claim 21, wherein said shrimp alkaline phosphatase is present in said composition in a concentration of at least 0.01 units of shrimp alkaline phosphatase per microliter.

37. A composition according to claim 22, said composition having a pH of 7 to 9.

38. A composition according to claim 22, said composition having a pH of about 7.5.

39. A composition according to claim 22, further comprising Tris-HCl.

40. A composition according to claim 39, comprising 5–100 mM Tris-HCl.

41. A composition according to claim 22, further comprising EDTA in a concentration of less than 100 mM.

42. A composition according to claim 22, further comprising DTT in a concentration of less than 250 mM.

43. A composition according to claim 22, said composition further comprising at least 20 volume percent of a stabilizer selected from the group consisting of glycerol, ethylene glycol and glycine.

44. A composition according to claim 22, wherein said Exonuclease I is present in said composition in a concentration of at least 0.1 units of Exonuclease I per microliter.

45. A composition according to claim 21, said shrimp alkaline phosphatase retaining at least 50% of its functional activity when said composition is stored at −20° C. for 24 hours.

46. A composition according to claim 21, said shrimp alkaline phosphatase retaining at least 50% of its functional activity when said composition is stored at −20° C. for 3 days.

47. A composition according to claim 21, said shrimp alkaline phosphatase retaining at least 50% of its functional activity when said composition is stored at 4° C. for 24 hours.

48. A composition according to claim 1, having a nuclease:phosphatase unit ratio of less than 50:1.

49. A composition according to claim 21, wherein said nuclease is Exonuclease I, said composition having an Exonuclease I:shrimp alkaline phosphatase unit ratio of less than about 10:1.

50. A composition according to claim 21, wherein said nuclease is Exonuclease I, said composition having an Exonuclease I:shrimp alkaline phosphatase unit ratio of less than about 5:1.

\* \* \* \* \*

UNITED STATES PATENT AND TRADEMARK OFFICE
CERTIFICATE OF CORRECTION

PATENT NO.    : 6,379,940 B2
DATED         : April 30, 2002
INVENTOR(S)   : Moffett et al.

It is certified that error appears in the above-identified patent and that said Letters Patent is hereby corrected as shown below:

Title page,
Item [56], References Cited, OTHER PUBLICATIONS, please delete:
"USB Corporation, Sequenase Version, 2.0 PCR Product Sequencing Kit, booklet, 1999." and insert therefor:
-- USB Corporation, Sequenase Version 2.0 PCR Product Sequencing Kit, booklet, 1999. --

Column 4,
Line 28, please delete "4$\mu$l" and insert therefor -- $\mu$l --.

Signed and Sealed this

Eighth Day of October, 2002

Attest:

Attesting Officer

JAMES E. ROGAN
Director of the United States Patent and Trademark Office